United States Patent
Zou et al.

(10) Patent No.: US 11,975,052 B2
(45) Date of Patent: May 7, 2024

(54) COMPOUND COMPOSITION FOR IMPROVING BONE HEALTH AND PREPARATION AND APPLICATION THEREOF

(71) Applicants: Chenland Nutritionals Inc., Pomona, CA (US); Qingdao Chenland Pharmaceutical Technology Development Co., Ltd., Qingdao (CN)

(72) Inventors: Shengcan Zou, Qingdao (CN); Zengliang Zhang, Qingdao (CN); Jiancheng Zong, Qingdao (CN); Wenyu Li, Qingdao (CN); Xin Li, Qingdao (CN); Li Li, Qingdao (CN); Shanglong Wang, Qingdao (CN); Lei Zong, Qingdao (CN)

(73) Assignees: Chenland Nutritionals Inc.; Qingdao Chenland Pharmaceutical Technology Development Co., Ltd., Qingdao (CN)

( * ) Notice: Subject to any disclaimer, the term of this patent is extended or adjusted under 35 U.S.C. 154(b) by 659 days.

(21) Appl. No.: 17/156,534

(22) Filed: Jan. 23, 2021

(65) Prior Publication Data
US 2022/0152162 A1   May 19, 2022

Related U.S. Application Data

(63) Continuation of application No. PCT/CN2020/130483, filed on Nov. 20, 2020.

(30) Foreign Application Priority Data

Nov. 17, 2020 (CN) .......................... 202011286878.8

(51) Int. Cl.
| | |
|---|---|
| *A61K 38/39* | (2006.01) |
| *A23J 3/34* | (2006.01) |
| *A23L 29/281* | (2016.01) |
| *A23L 33/00* | (2016.01) |
| *A23L 33/105* | (2016.01) |
| *A23L 33/155* | (2016.01) |
| *A23L 33/16* | (2016.01) |
| *A23L 33/17* | (2016.01) |
| *A61K 31/122* | (2006.01) |
| *A61K 31/593* | (2006.01) |
| *A61K 33/06* | (2006.01) |
| *A61K 36/126* | (2006.01) |
| *A61K 36/39* | (2006.01) |
| *A61K 36/46* | (2006.01) |
| *A61P 19/00* | (2006.01) |

(52) U.S. Cl.
CPC ............ *A61K 38/39* (2013.01); *A23L 29/284* (2016.08); *A23L 33/105* (2016.08); *A23L 33/155* (2016.08); *A23L 33/16* (2016.08); *A23L 33/17* (2016.08); *A23L 33/40* (2016.08); *A61K 31/122* (2013.01); *A61K 31/593* (2013.01); *A61K 33/06* (2013.01); *A61K 36/126* (2013.01); *A61K 36/39* (2013.01); *A61K 36/46* (2013.01); *A61P 19/00* (2018.01); *A23J 3/342* (2013.01); *A23V 2002/00* (2013.01); *A23V 2250/5422* (2013.01); *A61K 2236/31* (2013.01); *A61K 2236/333* (2013.01); *A61K 2236/37* (2013.01); *A61K 2236/51* (2013.01); *A61K 2236/53* (2013.01)

(58) Field of Classification Search
None
See application file for complete search history.

(56) References Cited

FOREIGN PATENT DOCUMENTS

CN    104312857    *    1/2015

\* cited by examiner

*Primary Examiner* — Michael V Meller

(57) ABSTRACT

A compound composition for improving bone health and preparation and application thereof are provided. The compound composition is prepared by combining a traditional Chinese medicine extract with chicken cartilage collagen, magnesium, vitamin K2 and vitamin D3. The compound composition overcomes the food safety risk of the existing osteoporosis preventive drugs by adding the traditional Chinese medicine extract for improving osteoporosis and promoting bone health. And the compound composition disclosed can be used as a dietary supplement or health food raw material for preventing or treating osteoporosis. Therefore, the compound composition disclosed is suitable for promotion and application.

1 Claim, 4 Drawing Sheets

COMPOUND COMPOSITION FOR IMPROVING BONE HEALTH AND PREPARATION AND APPLICATION THEREOF

TECHNICAL FIELD

The present disclosure relates to the technical field of natural medicine, and more particularly to a compound composition for improving bone health and preparation and application thereof, which is a traditional Chinese medicine compound composition for nourishing bones, assisting bone reconstruction and promoting bone health.

BACKGROUND

Osteoporosis (OP) is a kind of systemic bone disease, which is characterized by osteopenia, damage of bone microstructure, increase of bone fragility and fracture. With the aging of the world population, the prevalence of osteoporosis is increasing year by year. At present, more than 200 million of the world's population has osteoporosis, and its incidence rate has ranked sixth in the common and frequently occurring diseases. The amount of osteoporosis in China is over 90 million, ranking the highest in the world. The latest epidemiological survey results show that the prevalence of osteoporosis in the population aged 50 and over 65 in China has reached 19.2% and 32% respectively, which has become one of the common causes of death in the elderly. In addition, osteoporosis is considered as "invisible disease", and there are no obvious clinical symptoms in the early stage. Only when there are serious consequences such as fracture that cannot be reversed, can patients pay attention to it. Therefore, we should pay more attention to the early prevention of osteoporosis.

At present, the treatment of osteoporosis mainly starts from promoting bone formation and inhibiting bone resorption to regulate bone metabolism, but the large side effects often limit its wide application. For example, long-term use of estrogen can increase the risk of endometrial cancer and breast cancer. As well as the commonly used osteoporosis prevention method is to supplement calcium and vitamin D, but for some people, the effect of only appropriate supplement is not good, and excessive supplement may increase the risk of kidney stones and cardiovascular disease, so it is urgent to find more safe and effective osteoporosis prevention measures.

Given the above, there is an urgent need for those of ordinary skill in the art to develop a safe and effective compound composition for treating osteoporosis and promoting bone health.

SUMMARY

In view of the above, an object of the present disclosure is to provide a compound composition for improving bone health and application in preparation of health care products.

Technical solutions of the present disclosure are specifically described as follows.

In a first aspect, the present disclosure provides a compound composition for improving bone health, including:
0.8~0.15 g (30.768~68.179% by weight) of chicken cartilage collagen;
200~300 mg (6.249~18.750% by weight) of magnesium;
80~100 μg (0.002~0.0067% by weight) of vitamin k2;
2~15 μg (0.00006~0.00099% by weight) of vitamin D3;
0.5~1.5 g (21.738~59.998% by weight) of traditional Chinese medicine extract.

A compound composition disclosed for promoting bone health is obtained by combining a traditional Chinese medicine extract with chicken cartilage collagen, magnesium, vitamin K2 and vitamin D3. The compound composition overcomes the food safety risk of the existing osteoporosis preventive drugs by adding the traditional Chinese medicine extract to improve osteoporosis and promote bone health.

Preferably, the compound composition includes:
45.4525% by weight (1 g) of chicken cartilage collagen;
9.0905% by weight (200 mg) of magnesium;
0.004% by weight (90 μg) of vitamin k2;
0.0005% by weight (10 μg) of vitamin D3;
45.4525% by weight (1 g) of traditional Chinese medicine extract.

Further, the traditional Chinese medicine extract is prepared by extracting Chinese medicine, and the traditional Chinese medicine extract is a mixture of *Eucommia ulmoides* extract, Rhizoma Drynariae extract and Semen Cuscutae extract.

A traditional Chinese medicine extract raw material of the *Eucommia ulmoides* extract is *Eucommia* barks and *Eucommia* leaves, and a mass ratio of the *Eucommia* barks and the *Eucommia* leaves added is 2:1.

Further, the traditional Chinese medicine includes 1~300 parts by weight of *Eucommia* barks, 1~150 parts by weight of *Eucommia* leaves, 1-100 parts by weight of Rhizoma Drynariae, and 1-50 parts by weight of Semen Cuscutae.

It should be noted that, the raw materials of the extracts used herein are scientifically selected (based on prescriptions related to bone health) and combined organically according to the compatibility of traditional Chinese medicines rather than simple superimposing of the effect of each Chinese medicine. Effects of the abovementioned traditional Chinese medicine materials are listed as follows:

*Eucommia* leaves
Functions: invigorating liver and kidney, strengthening muscles and bones.
Indications: liver and kidney deficiency, dizziness, waist and knee pain, muscle and bone weakness.

*Eucommia* barks
Functions: invigorating liver and kidney, strengthening muscles and bones and preventing miscarriage;
Indications: lumbar spine pain, foot and knee weakness, dribbling urination, vaginal itch and wetness, fetal leakage, fetal restlessness and high blood pressure.

Rhizoma Drynariae
Functions: healing and relieving pain, invigorating the kidney and strengthening bones and external use to disperse wind and eliminate freckle.
Indications: sprain and contusion, bone fracture, kidney deficiency, low back pain, muscle and bone weakness, tinnitus and deafness, loose teeth and external treatment of alopecia areata and vitiligo.

Semen Cuscutae
Functions: replenishing liver and kidney, consolidating essence and reducing urination, preventing miscarriage, improving eyesight, stopping diarrhea and external use to eliminate wind and freckle.
Indications: liver and kidney deficiency, waist and knee weakness, impotence and nocturnal emission, enuresis, frequent urination, kidney deficiency, fetal leakage, fetal restlessness, dysopia, spleen and kidney deficiency and diarrhea and external use for vitiligo.

It can be seen from above that though *Eucommia* barks, *Eucommia* leaves, and Rhizoma Drynariae can strengthen muscles and bones, they still have their own emphasis. On this basis, *Eucommia* barks can strengthen the liver and kidney, and has the effect of treating lumbar spine pain, foot and knee weakness; Semen Cuscutae can replenish liver and kidney, and has the effect of eliminating wind and freckle, spleen and kidney deficiency and diarrhea, which is not simply superimposed with *Eucommia* barks and *Eucommia* leaves, but complement each other, and Rhizoma Drynariae has the effect of healing pain, tendon and bone fracture, and they are compatible with each other.

In addition, though the common dosage of each traditional Chinese medicine is known in the prior art, the prescription of the disclosure is made for the target disease by organically combining the above medicines, and its medicinal effect is not equivalent to the simple superposition of the effects of these medicines at a commonly-used amount. Actually, it cannot determine the amount of each medicine in the prescription according to their individual commonly-used amount, and the compounding ratio depends on many factors such as the characteristics of the medicinal materials and the compatibility of monarch drugs, ministerial drugs, adjuvant drugs and envoy drugs, and cannot be determined by experimental means such as comparison method and orthogonal test.

In a second aspect, the disclosure provides a method of preparing the above compound composition, including:
1) mixing the *Eucommia* barks and the *Eucommia* leaves in a mass ratio of 2:1, heating, refluxing and extracting with a 70-85% ethanol solution in a volume ratio of 1:8 for 2 h, and filtering to obtain a residue; adding a deionized water in a volume ratio of 1:6 to the residue, heating and refluxing twice each for 1 h and filtration; combining filtrates followed by purification and concentration, adding maltodextrin, and spray drying at 150-200° C. followed by sieving with a sieve of 80 mesh to obtain the *Eucommia ulmoides* extract; where the maltodextrin is 10% by weight of the *Eucommia* barks and the *Eucommia* leaves;
2) subjecting Rhizoma Drynariae to extraction with a 60%-80% ethanol solution in a volume ratio of 1:8 under refluxing for 2 h and filtration to obtain a residue; subjecting the residue to extraction with 70%-85% ethanol solution under refluxing twice each for 2 h and filtration; combining filtrates followed by concentration; adding maltodextrin and spray drying at 150-200° C. followed by sieving with a sieve of 80 mesh to obtain the Rhizoma Drynariae extract; where the maltodextrin is 10% by weight of Rhizoma Drynariae;
3) subjecting Semen Cuscutae to immersion in a 40%-80% ethanol solution in a volume ratio of 1:8 for 30 min, extraction under refluxing for 2 h and filtration to obtain a residue; subjecting the residue to extraction with a 40%-80% ethanol solution a volume ratio of 1:6 under refluxing 2~3 times each for 2 h and filtration; combining filtrates followed by concentration and subjecting the concentrated product to spray drying at 150-200° C. followed by sieving with a sieve of 80 mesh to produce the Semen Cuscutae extract;
4) mixing the *Eucommia ulmoides* extract, the Rhizoma Drynariae extract and the Semen Cuscutae extract uniformly to produce a traditional Chinese medicine extract; and
5) adding chicken cartilage collagen, magnesium, vitamin K2 and vitamin D3 into the traditional Chinese medicine extract and mixing to prepare the compound composition.

Preferably, the traditional Chinese medicine extract includes:
60-80% by weight of *Eucommia* extract;
10-40% by weight of Rhizoma Drynariae extract;
5-10% by Semen Cuscutae extract.

And, a mixture ratio of the traditional Chinese medicine extract, the chicken cartilage collagen, the magnesium, the vitamin K2 and the vitamin D3 is
30.768~68.179% by weight of chicken cartilage collagen;
6.249~18.750% by weight of magnesium;
0.002~0.0067% by weight of vitamin k2;
0.00006~0.00099% by weight of vitamin D3;
21.738~59.998% by weight of traditional Chinese medicine extract.

In a third aspect, the disclosure further provides an application of the compound composition for improving bone health in the preparation of a health food.

The compound composition of the present disclosure is used as a dietary supplement or a health care food raw material for preventing or treating moderate and mild osteoporosis.

Compared with the prior art, the disclosure has the following beneficial effects.

1) Traditional Chinese medicine scholars propose that the pathogenesis of osteoporosis is closely associated with "kidney deficiency", and *Eucommia ulmoides*, Rhizoma Drynariae and Semen Cuscutae have the effects of invigorating the liver and kidney and strengthening the bones and muscles, so these medicinal materials are commonly used in clinic for strengthening the kidney and bones and exhibit good therapeutic effects. *Eucommia ulmoides*, Rhizoma Drynariae and Semen Cuscutae have been used in combination, which has been proved to be effective in treating osteoporosis and promoting bone health. On the basis of traditional Chinese medicine compatibility theory, the disclosure innovates *Eucommia ulmoides*, Rhizoma Drynariae and Semen Cuscutae to design an optimal proportion composition with the function of improving osteoporosis and promoting bone health. By combining collagen, magnesium, vitamin K and vitamin D with traditional Chinese medicine composition, the compound composition can really nourish bone, help bone reconstruction, and introduce calcium into bone, making bone dense and strong.

2) The disclosure employs a preparation process of separate extraction and compounding, and determines the main active substances in each extract. Compared to the traditional extraction process, the disclosure has better quality of the extract and higher controllability.

3) The compound composition of the disclosure is confirmed by pharmacological experiment to have desirable effects of nourishing bone, helping bone reconstruction, improving osteoporosis and bone health.

4) The compound composition provided herein has no toxic side effects and high adsorption. The traditional Chinese medicine extract for treating osteoporosis and promoting bone health can not only improve the bone health of middle-aged and elderly people, but also effectively avoid other concurrent diseases caused by osteoporosis.

BRIEF DESCRIPTION OF THE DRAWINGS

The drawings used in the embodiments will be briefly described to make the technical solutions of the disclosure clearer. Obviously, the embodiments illustrated in the drawings are merely part of the embodiments of the disclosure, and other drawings obtained by those skilled in the art without sparing any creative effort should fall within the scope of the invention.

DETAILED DESCRIPTION OF EMBODIMENTS

Figure 1:
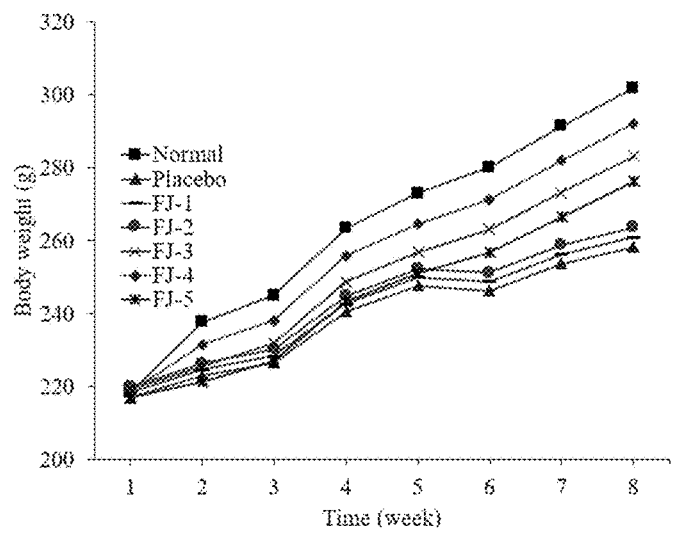
FIG. 1 shows the results of dynamic weight measurement of rats in each group (n=8)
Figure 2:
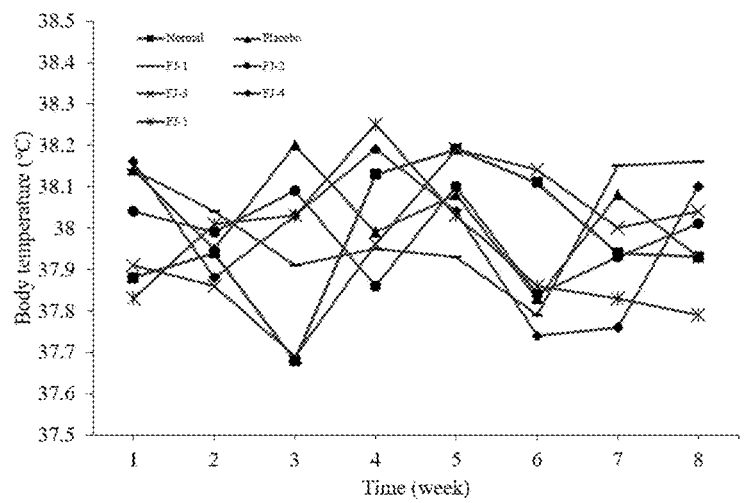
FIG. 2 shows dynamic body temperature of rats in each group (n=8).
Figure 3:
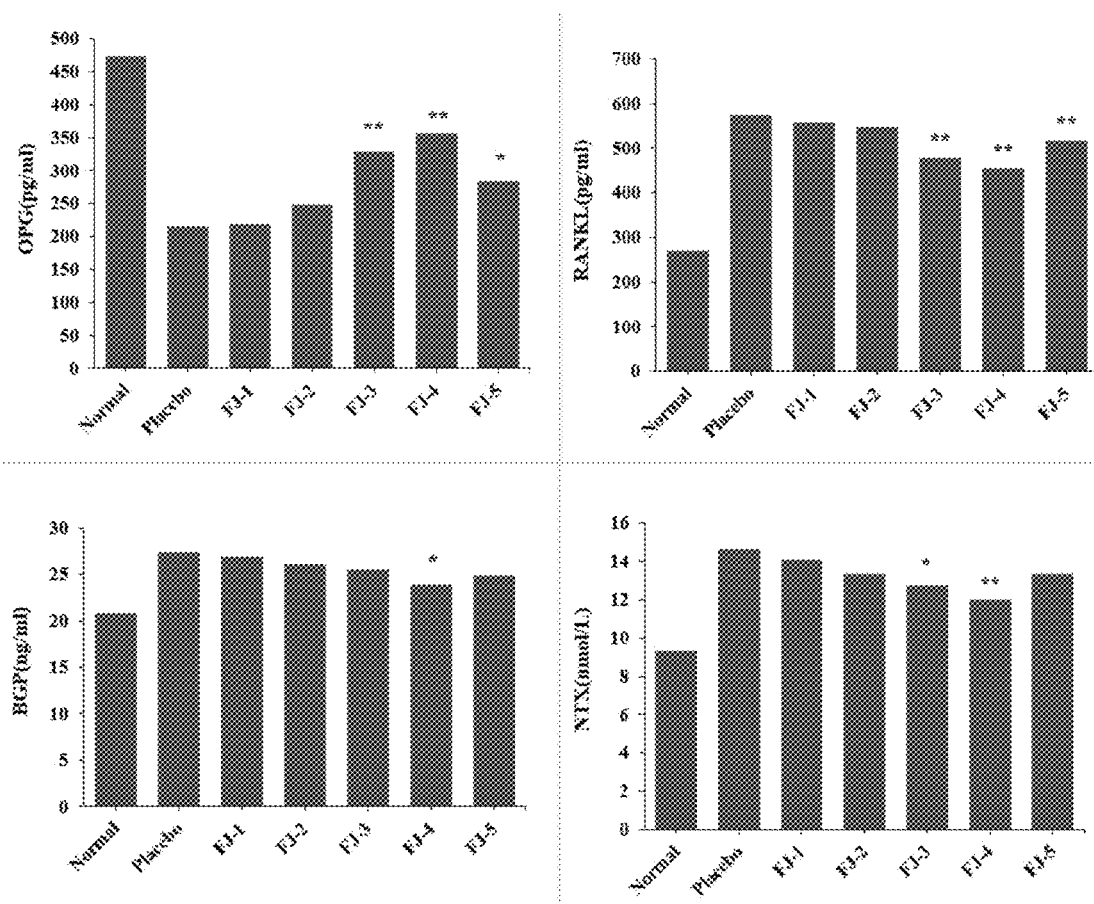
FIG. 3 shows results of final blood test of rats in each group (n=8).
Figure 4:
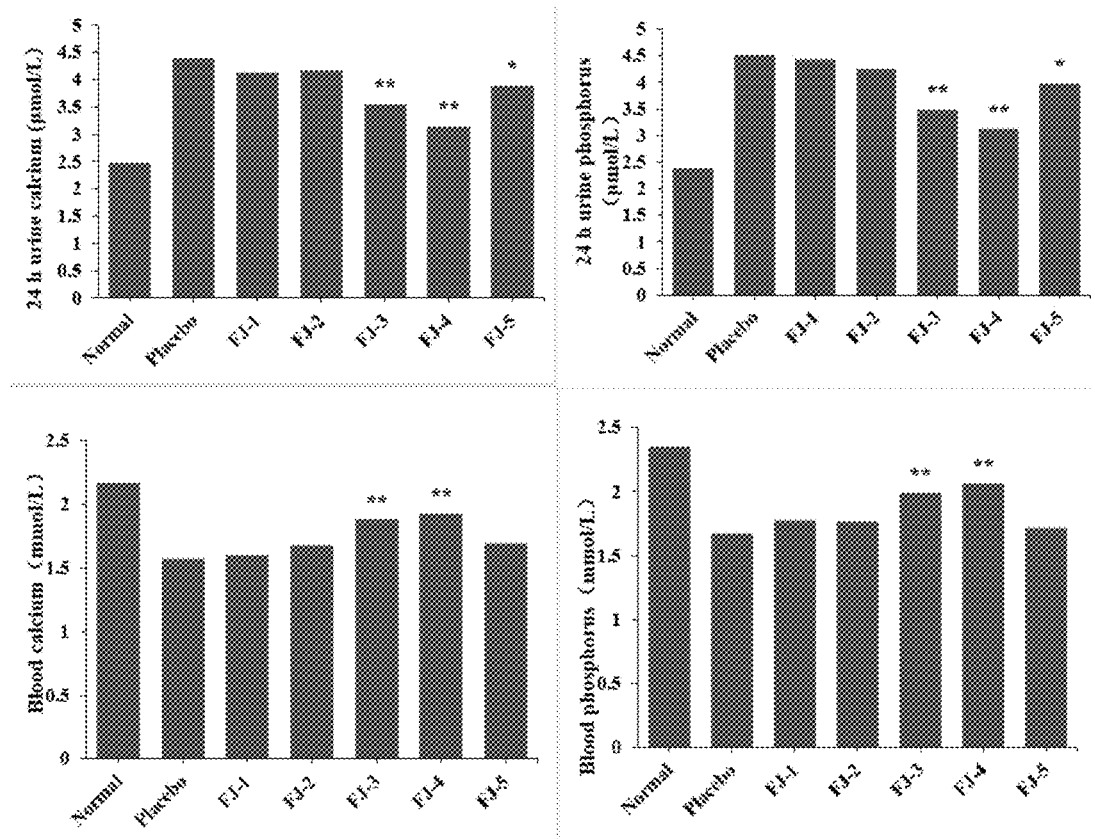
FIG. 4 shows results of final biochemical indexes of rats in each group (n=8).

Technical solutions of the present disclosure will be clearly and completely described below with reference to the embodiments. Obviously, described below are merely some embodiments of the disclosure, which are not intended to limit the disclosure. Other embodiments made by those skilled in the art without sparing any creative effort should fall within the scope of the disclosure.

The embodiments of the disclosure provide a safe and effective compound composition, which can treat or prevent osteoporosis and promote bone health, and can be used as a dietary supplement or health food raw material for the prevention or treatment of moderate and mild osteoporosis.

The disclosure will be further described below with reference to the embodiments. It should be understood that these embodiments are merely illustrative of the disclosure, and are not intended to limit the disclosure. Any improvement and modification made by those skilled in the art without departing from the spirit of the invention should still fall within the scope of the disclosure.

The technical scheme of the disclosure will be further described in combination with specific embodiments.

Embodiment 1

The disclosure provides a compound composition for improving bone health, including:
44.0200% by weight of chicken cartilage collagen;
9.9700% by weight of magnesium;
0.0035% by weight of vitamin k2;
0.0005% by weight of vitamin D3;
46.0060% by weight of traditional Chinese medicine extract.

Embodiment 2

The disclosure provides a compound composition for improving bone health, including:
41.910% by weight of chicken cartilage collagen;
10.006% by weight of magnesium;
0.003% by weight of vitamin k2;
0.0002% by weight of vitamin D3;
48.0808% by weight of traditional Chinese medicine extract.

Embodiment 3

The disclosure provides a compound composition for improving bone health, including:
41.880% by weight of chicken cartilage collagen;
8.114% by weight of magnesium;
0.004% by weight of vitamin k2;
0.0006% by weight of vitamin D3;
50.0014% by weight of traditional Chinese medicine extract.

Embodiment 4

The disclosure provides a compound composition for improving bone health, including:
40.720% by weight of chicken cartilage collagen;
8.008% by weight of magnesium;
0.0010% by weight of vitamin k2;
0.0005% by weight of vitamin D3;
51.2705% by weight of traditional Chinese medicine extract.

Embodiment 5

The disclosure provides a compound composition for improving bone health, including:
48.318% by weight of chicken cartilage collagen;
8.040% by weight of magnesium;
0.001% by weight of vitamin k2;
0.0001% by weight of vitamin D3;
43.6409% by weight of traditional Chinese medicine extract.

Embodiment 6

The composition of the traditional Chinese medicine used in the traditional Chinese medicine extract of the compound composition for improving bone health disclosed in the above embodiments 1~5, by weight parts:
there were 100 *Eucommia* barks, 50 *Eucommia* leaves, 25 Rhizoma Drynariae and 8 Semen Cuscutae.

The preparation method of the traditional Chinese medicine extract was as follows. Each herb was extracted by alcohol extraction process, purified by macroporous resin, concentrated and spray dried to obtain the traditional Chinese medicine extract.

Specifically, the preparation method of the compound composition for improving bone health included following steps:

1) Each herb was extracted by alcohol extraction process, purified by macroporous resin, concentrated and spray dried to obtain the traditional Chinese medicine extract.

2) The prepared traditional Chinese medicine extract was evenly mixed with chicken cartilage collagen, magnesium, vitamin K2 and vitamin D3 to obtain the compound composition.

Embodiment 7

The composition of the Chinese herbal medicine used in the traditional Chinese medicine extract of the compound composition for improving bone health disclosed in the above embodiments 1~5, by weight parts:
there were 60 *Eucommia* barks, 30 *Eucommia* leaves, 20 Rhizoma Drynariae and 5 Semen Cuscutae.

The preparation method of the traditional Chinese medicine extract was as follows. Each herb was extracted by alcohol extraction process, purified by macroporous resin, concentrated and spray dried to obtain the traditional Chinese medicine extract.

Specifically, the preparation method of the compound composition for improving bone health included the following steps:

1) Each herb was extracted by alcohol extraction process, purified by macroporous resin, concentrated and spray dried to obtain the traditional Chinese medicine extract.

2) The prepared traditional Chinese medicine extract was evenly mixed with chicken cartilage collagen, magnesium, vitamin K2 and vitamin D3 to obtain the compound composition.

Embodiment 8

The composition of the Chinese herbal medicine used in the traditional Chinese medicine extract of the compound composition for improving bone health disclosed in the above embodiments 1~5, by weight parts:
there were 80 *Eucommia* barks, 40 *Eucommia* leaves, 10 Rhizoma Drynariae and 3 Semen Cuscutae.

The preparation method of the traditional Chinese medicine extract was as follows. Each herb was extracted by alcohol extraction process, purified by macroporous resin, concentrated and spray dried to obtain the traditional Chinese medicine extract.

Specifically, the preparation method of the compound composition for improving bone health included the following steps:

1) Each herb was extracted by alcohol extraction process, purified by macroporous resin, concentrated and spray dried to obtain the traditional Chinese medicine extract.

2) The prepared traditional Chinese medicine extract was evenly mixed with chicken cartilage collagen, magnesium, vitamin K2 and vitamin D3 to obtain the compound composition.

Exemplary, the above disclosed preparation method of a compound composition for improving bone health and the preparation method of traditional Chinese medicine extract thereof are referred to the following examples for details.

Embodiment 9

A traditional Chinese medicine extract of a compound composition for improving bone health included *Eucommia* barks, Rhizoma Drynariae and Semen Cuscutae.

And, the preparation method of the traditional Chinese medicine extract included following steps:

1) *Eucommia* barks was subjected to extraction with an 80% ethanol solution in a volume ratio of 1:6 for 2 h and filtration to obtain a residue. The residue was subjected to extraction with deionized water twice in a volume ratio of 1:6 under refluxing each for 1.5 h and filtration. Filtrates were combined, concentrated and added with maltodextrin, where the maltodextrin was 5% by weight of the *Eucommia* barks. The combined filtrate was continuously concentrated to a density of 1.15-1.2, spray dried at 200° C. and sieved with a sieve of 80 mesh to produce the *Eucommia ulmoides* extract.

2) Rhizoma Drynariae was crushed and subjected to extraction with a 75% ethanol solution three times respectively in a volume ratio of 1:6, 1:5 and 1:5 under refluxing each for 2 h and filtration. Filtrates were combined, concentrated and added with maltodextrin, where the maltodextrin was 10% by weight of Rhizoma Drynariae. Then the combined filtrate was continuously concentrated to a density of 1.2, spray dried at 200° C. and sieved with a sieve of 80 mesh to produce the Rhizoma Drynariae extract.

3) Semen Cuscutae was subjected to extraction with a 75% ethanol solution three times respectively in a volume ratio of 1:6, 1:5 and 1:5 under refluxing each for 2 h and filtration. Filtrates were combined, concentrated to a density of 1.12-1.15 and subjected to spray drying at 180° C. The dried product was sieved with a sieve of 80 mesh to produce the Semen Cuscutae extract.

4) The *Eucommia ulmoides* extract, the Rhizoma Drynariae extract and the Semen Cuscutae extract were mixed uniformly in a weight ratio of 60%:30%:10% to produce the traditional Chinese medicine extract.

Embodiment 10

A traditional Chinese medicine extract of a compound composition for improving bone health included *Eucommia* barks, *Eucommia* leaves, Rhizoma Drynariae and Semen Cuscutae.

And, the preparation method of the traditional Chinese medicine extract included following steps:

1) *Eucommia* barks and *Eucommia* leaves were mixed in a ratio of 2:1. The *Eucommia* mixture was subjected to extraction with a 75% ethanol solution in a volume ratio of 1:6 for 2 h and filtration to obtain a residue. The residue was subjected to extraction with deionized water twice in a volume ratio of 1:6 under refluxing each for 1.5 h and filtration. Filtrates were combined, concentrated and added with maltodextrin, where the maltodextrin was 5% by weight of the *Eucommia* barks and *Eucommia* leaves. The combined filtrate was continuously concentrated to a density of 1.15-1.2, spray dried at 200° C. and sieved with a sieve of 80 mesh to produce the *Eucommia ulmoides* extract.

2) Rhizoma Drynariae was crushed and subjected to extraction with a 75% ethanol solution three times respectively in a volume ratio of 1:6, 1:5 and 1:5 under refluxing each for 2 h and filtration. Filtrates were combined, concentrated and added with maltodextrin, where the maltodextrin was 10% by weight of Rhizoma Drynariae. Then the combined filtrate was continuously concentrated to a density of 1.2, spray dried at 200° C. and sieved with a sieve of 80 mesh to produce the Rhizoma Drynariae extract.

3) Semen Cuscutae was subjected to extraction with a 50% ethanol solution three times respectively in a volume ratio of 1:6, 1:5 and 1:5 under refluxing each for 2 h and filtration. Filtrates were combined, concentrated to a density of 1.12-1.15 and subjected to spray drying at 180° C. The dried product was sieved with a sieve of 80 mesh to produce the Semen Cuscutae extract.

4) The *Eucommia ulmoides* extract, the Rhizoma Drynariae extract and the Semen Cuscutae extract were mixed uniformly in a weight ratio of 60%:30%:10% to produce the traditional Chinese medicine extract.

Embodiment 11

A traditional Chinese medicine extract of a compound composition for improving bone health included *Eucommia* barks, *Eucommia* leaves, Rhizoma Drynariae and Semen Cuscutae.

And, the preparation method of the traditional Chinese medicine extract included following steps:

1) *Eucommia* barks and *Eucommia* leaves were mixed in a ratio of 2:1. The *Eucommia* mixture was subjected to extraction with a 70% ethanol solution in a volume ratio of 1:6 for 2 h and filtration to obtain a residue. The residue was subjected to extraction with deionized water twice in a volume ratio of 1:6 under refluxing each for 1.5 h and filtration. Filtrates were combined, concentrated and added with maltodextrin, where the maltodextrin was 5% by weight of the *Eucommia* barks and *Eucommia* leaves. The combined filtrate was continuously concentrated to a density of 1.15-1.2, spray dried at 180° C. and sieved with a sieve of 80 mesh to produce the *Eucommia ulmoides* extract.

2) Rhizoma Drynariae was crushed and subjected to extraction with an 80% ethanol solution three times respectively in a volume ratio of 1:6, 1:5 and 1:5 under refluxing each for 2 h and filtration. Filtrates were combined, concentrated and added with maltodextrin, where the maltodextrin was 10% by weight of Rhizoma Drynariae. Then the combined filtrate was continuously concentrated to a density of 1.2, spray dried at 180° C. and sieved with a sieve of 80 mesh to produce the Rhizoma Drynariae extract.

3) Semen Cuscutae was subjected to extraction with an 80% ethanol solution three times respectively in a volume ratio of 1:6, 1:5 and 1:5 under refluxing each for 2 h and filtration. Filtrates were combined, concentrated to a density of 1.12-1.15 and subjected to spray drying at 180° C. The dried product was sieved with a sieve of 80 mesh to produce the Semen Cuscutae extract.

4) The *Eucommia ulmoides* extract, the Rhizoma Drynariae extract and the Semen Cuscutae extract were mixed uniformly in a weight ratio of 75%:15%:10% to produce the traditional Chinese medicine extract.

Embodiment 12

A traditional Chinese medicine extract of a compound composition for improving bone health included *Eucommia* barks, *Eucommia* leaves, Rhizoma Drynariae and Semen Cuscutae, chicken cartilage collagen, magnesium, vitamin k2, vitamin D3.

And, the preparation method of the traditional Chinese medicine extract included following steps:

1) *Eucommia* barks and *Eucommia* leaves were mixed in a ratio of 2:1. The *Eucommia* mixture was subjected to extraction with a 75% ethanol solution in a volume ratio of 1:6 for 2 h and filtration to obtain a residue. The residue was subjected to extraction with deionized water twice in a volume ratio of 1:6 under refluxing each for 1.5 h and filtration. Filtrates were combined, concentrated and added with maltodextrin, where the maltodextrin was 5% by weight of the *Eucommia* barks and *Eucommia* leaves. The combined filtrate was continuously concentrated to a density of 1.15-1.2, spray dried at 200° C. and sieved with a sieve of 80 mesh to produce the *Eucommia ulmoides* extract.

2) Rhizoma Drynariae was crushed and subjected to extraction with an 75% ethanol solution three times respectively in a volume ratio of 1:6, 1:5 and 1:5 under refluxing each for 2 h and filtration. Filtrates were combined, concentrated and added with maltodextrin, where the maltodextrin was 10% by weight of Rhizoma Drynariae. Then the combined filtrate was continuously concentrated to a density of 1.2, spray dried at 200° C. and sieved with a sieve of 80 mesh to produce the Rhizoma Drynariae extract.

3) Semen Cuscutae was subjected to extraction with an 50% ethanol solution three times respectively in a volume ratio of 1:6, 1:5 and 1:5 under refluxing each for 2 h and filtration. Filtrates were combined, concentrated to a density of 1.12-1.15 and subjected to spray drying at 180° C. The dried product was sieved with a sieve of 80 mesh to produce the Semen Cuscutae extract.

4) The *Eucommia ulmoides* extract, the Rhizoma Drynariae extract and the Semen Cuscutae extract were mixed uniformly in a weight ratio of 60%:30%:10% to produce the traditional Chinese medicine extract.

5) The compound composition was obtained by adding chicken cartilage collagen, magnesium, vitamin K2 and vitamin D3 into the prepared traditional Chinese medicine extract, in which the traditional Chinese medicine extract accounted for 45.4525%, chicken cartilage collagen 45.4525%, magnesium 9.0905%, vitamin K2 0.004% and vitamin D3 0.0005%.

Embodiment 13

A traditional Chinese medicine extract of a compound composition for improving bone health included *Eucommia* barks, *Eucommia* leaves, Rhizoma Drynariae and Semen Cuscutae, chicken cartilage collagen, magnesium, vitamin k2, vitamin D3. And, the preparation method of the traditional Chinese medicine extract included following steps:

1) *Eucommia* barks and *Eucommia* leaves were mixed in a ratio of 2:1. The *Eucommia* mixture was subjected to extraction with a 70% ethanol solution in a volume ratio of 1:6 for 2 h and filtration to obtain a residue. The residue was subjected to extraction with deionized water twice in a volume ratio of 1:6 under refluxing each for 1.5 h and filtration. Filtrates were combined, concentrated and added with maltodextrin, where the maltodextrin was 5% by weight of the *Eucommia* barks and *Eucommia* leaves. The combined filtrate was continuously concentrated to a density of 1.15-1.2, spray dried at 200° C. and sieved with a sieve of 80 mesh to produce the *Eucommia ulmoides* extract.

2) Rhizoma Drynariae was crushed and subjected to extraction with an 80% ethanol solution three times respectively in a volume ratio of 1:6, 1:5 and 1:5 under refluxing each for 2 h and filtration. Filtrates were combined, concentrated and added with maltodextrin, where the maltodextrin was 10% by weight of Rhizoma Drynariae. Then the combined filtrate was continuously concentrated to a density of 1.2, spray dried at 200° C. and sieved with a sieve of 80 mesh to produce the Rhizoma Drynariae extract.

3) Semen Cuscutae was subjected to extraction with an 80% ethanol solution three times respectively in a volume ratio of 1:6, 1:5 and 1:5 under refluxing each for 2 h and filtration. Filtrates were combined, concentrated to a density of 1.12-1.15 and subjected to spray drying at 180° C. The dried product was sieved with a sieve of 80 mesh to produce the Semen Cuscutae extract.

4) The *Eucommia ulmoides* extract, the Rhizoma Drynariae extract and the Semen Cuscutae extract were mixed uniformly in a weight ratio of 75%:15%:10% to produce the traditional Chinese medicine extract.

5) The compound composition was obtained by adding chicken cartilage collagen, magnesium, vitamin K2 and vitamin D3 into the prepared traditional Chinese medicine extract, in which the traditional Chinese medicine extract accounted for 45.4525%, chicken cartilage collagen 45.4525%, magnesium 9.0905%, vitamin K2 0.004% and vitamin D3 0.0005%.

Embodiment 14

Preparation of Capsules

A traditional Chinese medicine extract of a compound composition for improving bone health included *Eucommia* barks, *Eucommia* leaves, Rhizoma Drynariae and Semen Cuscutae, chicken cartilage collagen, magnesium, vitamin k2, vitamin D3.

And, the preparation method of the traditional Chinese medicine extract included following steps:

1) *Eucommia* barks and *Eucommia* leaves were mixed in a ratio of 2:1. The *Eucommia* mixture was subjected to extraction with a 75% ethanol solution in a volume ratio of 1:6 for 2 h and filtration to obtain a residue. The residue was subjected to extraction with deionized water twice in a volume ratio of 1:6 under refluxing each for 1.5 h and filtration. Filtrates were combined, concentrated and added with maltodextrin, where the maltodextrin was 5% by weight of the *Eucommia* barks and *Eucommia* leaves. The combined filtrate was continuously concentrated to a density of 1.15-1.2, spray dried at 200° C. and sieved with a sieve of 80 mesh to produce the *Eucommia ulmoides* extract.

2) Rhizoma Drynariae was crushed and subjected to extraction with an 80% ethanol solution three times respectively in a volume ratio of 1:6, 1:5 and 1:5 under refluxing each for 2 h and filtration. Filtrates were combined, concentrated and added with maltodextrin, where the maltodextrin was 10% by weight of Rhizoma Drynariae. Then the combined filtrate was continuously concentrated to a density of 1.2, spray dried at 200° C. and sieved with a sieve of 80 mesh to produce the Rhizoma Drynariae extract.

3) Semen Cuscutae was subjected to extraction with an 50% ethanol solution three times respectively in a volume ratio of 1:6, 1:5 and 1:5 under refluxing each for 2 h and filtration. Filtrates were combined, concentrated to a density of 1.12-1.15 and subjected to spray drying at 180° C. The dried product was sieved with a sieve of 80 mesh to produce the Semen Cuscutae extract.

The prepared *Eucommia ulmoides* extract, the prepared Rhizoma Drynariae extract and the prepared Semen Cuscutae extract were mixed uniformly in a weight ratio of 60%:30%:10% to produce the traditional Chinese medicine extract.

4) The compound composition was obtained by adding chicken cartilage collagen, magnesium, vitamin K2 and vitamin D3 into the prepared traditional Chinese medicine extract, in which the traditional Chinese medicine extract accounted for 45.4525%, chicken cartilage collagen 45.4525%, magnesium 9.0905%, vitamin K2 0.004% and vitamin D3 0.0005%.

5) The compound composition obtained by the above preparation was evenly mixed and sieved with a sieve of 80 mesh. The pregelatinized starch, the talc magnesium stearate and the compound composition were mixed uniformly and capsuled, and the capsules were prepared.

Embodiment 15

Preparation of Tablets

A traditional Chinese medicine extract of a compound composition for improving bone health included *Eucommia* barks, *Eucommia* leaves, Rhizoma Drynariae and Semen Cuscutae, chicken cartilage collagen, magnesium, vitamin k2, vitamin D3.

And, the preparation method of the traditional Chinese medicine extract included following steps:

1) *Eucommia* barks and *Eucommia* leaves were mixed in a ratio of 2:1. The *Eucommia* mixture was subjected to extraction with a 75% ethanol solution in a volume ratio of 1:6 for 2 h and filtration to obtain a residue. The residue was subjected to extraction with deionized water twice in a volume ratio of 1:6 under refluxing each for 1.5 h and filtration. Filtrates were combined, concentrated and added with maltodextrin, where the maltodextrin was 5% by weight of the *Eucommia* barks and *Eucommia* leaves. The combined filtrate was continuously concentrated to a density of 1.15-1.2, spray dried at 200° C. and sieved with a sieve of 80 mesh to produce the *Eucommia ulmoides* extract.

2) Rhizoma Drynariae was crushed and subjected to extraction with an 80% ethanol solution three times respectively in a volume ratio of 1:6, 1:5 and 1:5 under refluxing each for 2 h and filtration. Filtrates were combined, concentrated and added with maltodextrin, where the maltodextrin was 10% by weight of Rhizoma Drynariae. Then the combined filtrate was continuously concentrated to a density of 1.2, spray dried at 200° C. and sieved with a sieve of 80 mesh to produce the Rhizoma Drynariae extract.

3) Semen Cuscutae was subjected to extraction with an 50% ethanol solution three times respectively in a volume ratio of 1:6, 1:5 and 1:5 under refluxing each for 2 h and filtration. Filtrates were combined, concentrated to a density of 1.12-1.15 and subjected to spray drying at 180° C. The dried product was sieved with a sieve of 80 mesh to produce the Semen Cuscutae extract.

4) The prepared *Eucommia ulmoides* extract, the prepared Rhizoma Drynariae extract and the prepared Semen Cuscutae extract were mixed uniformly in a weight ratio of 60%:30%:10% to produce the traditional Chinese medicine extract.

5) The compound composition was obtained by adding chicken cartilage collagen, magnesium, vitamin K2 and vitamin D3 into the prepared traditional Chinese medicine extract, in which the traditional Chinese medicine extract accounted for 45.4525%, chicken cartilage collagen 45.4525%, magnesium 9.0905%, vitamin K2 0.004% and vitamin D3 0.0005%.

6) The compound composition by the above preparation was evenly mixed and sieved with a sieve of 80 mesh to obtain a traditional Chinese medicine extract. Then the starch and the magnesium stearate were added and mixed uniformly, compressed into a sheet, coated with a film, and made into tablets.

Embodiment 16

Preparation of Granules

A traditional Chinese medicine extract of a compound composition for improving bone health included *Eucommia* barks, *Eucommia* leaves, Rhizoma Drynariae and Semen Cuscutae, chicken cartilage collagen, magnesium, vitamin k2, vitamin D3.

And, the preparation method of the traditional Chinese medicine extract included following steps:

1) *Eucommia* barks and *Eucommia* leaves were mixed in a ratio of 2:1. The *Eucommia* mixture was subjected to extraction with a 75% ethanol solution in a volume ratio of 1:6 for 2 h and filtration to obtain a residue. The residue was subjected to extraction with deionized water twice in a volume ratio of 1:6 under refluxing each for 1.5 h and filtration. Filtrates were combined, concentrated and added with maltodextrin, where the maltodextrin was 5% by weight of the *Eucommia* barks and *Eucommia* leaves. The combined filtrate was continuously concentrated to a density of 1.15-1.2 to produce the *Eucommia ulmoides* extracting solution.

2) Rhizoma Drynariae was crushed and subjected to extraction with an 80% ethanol solution three times respectively in a volume ratio of 1:6, 1:5 and 1:5 under refluxing each for 2 h and filtration. Filtrates were combined, concentrated and added with maltodextrin, where the maltodextrin was 10% by weight of Rhizoma Drynariae. Then the combined filtrate was continuously concentrated to a density of 1.2 to produce the Rhizoma Drynariae extracting solution.

3) Semen Cuscutae was subjected to extraction with an 50% ethanol solution three times respectively in a volume ratio of 1:6, 1:5 and 1:5 under refluxing each for 2 h and filtration. Filtrates were combined, concentrated to a density of 1.12-1.15 to produce the Semen Cuscutae extracting solution.

4) The prepared extracting solutions were evenly mixed and boiled to 1 g/ml to obtain an extract;

5) The boiled extract by the above preparation is put into a beaker, and the weighed chicken cartilage collagen, magnesium, vitamin D3, vitamin K2, vitamin D3, sucrose, starch and dextrin were added, mixed evenly, and stirred until it was kneaded into a ball by hand which would disperse if touched. The granules that cannot pass the 20 mesh sieve and 80 mesh sieve but can pass the 10 mesh sieve were selected and then put into the oven to dry in time and collect for standby.

6) The prepared granules were put into a vacuum dryer for drying, and the water content of the granules was controlled at 4%. The compound granules for improving bone health were prepared.

The content of the disclosure is not limited to the contents of the above-mentioned embodiments, and the combination of one or several embodiments can also realize the purpose of the disclosure.

In order to further verify the excellent effect of the invention, the following pharmacodynamic tests were carried out, where the drug to be experimented included Embodiment 9 group, Embodiment 10 group, Embodiment 12 group and competitive drug group.

1. Experiment Method:

Sixty-four Wistar rats were divided into 7 groups including normal group, negative group, competitive drug group, Embodiment 9 group with a low dose, and Embodiment 9 group with a high dose, Embodiment 12 group and Example 10 group. Four rats were fed in separate cages, two cages in each group, and were used for the establishment of osteoporosis model and evaluation of preventive administration after 7 days of adaptive growth without abnormal conditions.

2. Modeling:

According to the method described in the preparation and application of the medical experimental animal model and the standard operating procedure for the establishment of the model of osteoporosis in the model animal center, the method for establishing the model is as follows.

(1) The rats in each model group were fixed, and prednisone injection was aspirated by sterile syringe.

(2) Prednisone was given intramuscularly at the dose of 4.5 mg/kg twice a week for 8 weeks.

(3) The rats in the normal control group were treated with 0.2 ml normal saline.

(4) After the injection, the rats were fed normally and observed daily.

3. Administration:

The intragastric administration concentration of each group was shown in the table below. Each rat was given intragastric administration once a day from the day of modeling. The negative group was given intragastric administration of the equal volume drug solution (normal saline) every day for 8 weeks, that is, 56 days.

| Group | Group mark | Dosage | Drug concentration |
|---|---|---|---|
| normal group | Normal | / | / |
| negative group | Placebo | / | Equal volume drug solution |
| competitive drug group | FJ-1 | 90 | 30 mg/ml |
| Embodiment 9 group with a low dose | FJ-2 | 90 | 30 mg/ml |
| Embodiment 9 group with a high dose | FJ-3 | 180 | 60 mg/ml |
| Embodiment 12 group | FJ-4 | 214 | 70 mg/ml |
| Embodiment 10 group | FJ-5 | 135 | 45 mg/ml |

4. Experiment Results 4.1 Body Weight and Body Temperature Dynamic Test Results During the dynamic detection of body weight and body temperature, there was no significant difference in the change of body temperature among the groups. There were significant differences in weight gain among different groups. The body weight of the rats in the model group increased slowly, and the weight of each administration group was significantly lower than that of the normal control group. Compared with the model groups, there was no significant difference in FJ-1 and FJ-2 of administration groups, and the body weight gain of FJ-3, FJ-4, FJ-5 had significant improvement.

TABLE 1

Dynamic test results of body weight of rats in each group (n = 8)

| week | 1 | 2 | 3 | 4 | 5 | 6 | 7 | 8 |
|---|---|---|---|---|---|---|---|---|
| Normal | 218.45 ± 14.8 | 237.81 ± 17.74 | 245.04 ± 19.29 | 263.54 ± 21.83 | 273.04 ± 23.75 | 280.18 ± 25.12 | 291.54 ± 26.83 | 301.95 ± 27.67 |
| Placebo | 217.08 ± 10.74 | 223.11 ± 12.23 | 226.58 ± 12.97 | 240.61 ± 14.85 | 247.71 ± 16.11 | 246.4 ± 17.03 | 253.71 ± 18.36 | 258.4 ± 20.11 |
| FJ-1 | 218.56 ± 12.42 | 224.83 ± 14.14 | 228.45 ± 15.23 | 242.74 ± 18.69 | 250.03 ± 20.35 | 248.84 ± 21.53 | 256.3 ± 23.18 | 261.08 ± 25.04 |
| FJ-2 | 220.08 ± 13.43 | 226.54 ± 15.3 | 230.3 ± 17.72 | 244.84 ± 21.57 | 252.34 ± 23.2 | 251.29 ± 24.54 | 258.94 ± 26.5 | 263.79 ± 29.92 |
| FJ-3 | 219.39 ± 18.53 | 225.76 ± 21.12 | 231.96 ± 22.97 | 248.74 ± 26.02 | 256.94 ± 28.31 | 263.14 ± 29.94 | 273.35 ± 31.98 | 283.19 ± 32.98 |
| FJ-4 | 218.9 ± 15.92 | 231.59 ± 18.46 | 238.25 ± 20.07 | 255.86 ± 22.74 | 264.68 ± 24.73 | 271.34 ± 26.16 | 282.08 ± 27.94 | 292.2 ± 28.81 |
| FJ-5 | 217.26 ± 15.44 | 221.36 ± 17.58 | 227.15 ± 19.13 | 243.28 ± 21.67 | 251 ± 23.56 | 256.88 ± 24.93 | 266.66 ± 26.62 | 276.3 ± 27.44 |

TABLE 2

Dynamic test results of body temperature of rats in each group (n = 8)

|  | 1 | 2 | 3 | 4 | 5 | 6 | 7 | 8 |
|---|---|---|---|---|---|---|---|---|
| Normal | 37.88 ± 0.37 | 37.94 ± 0.4 | 37.68 ± 0.24 | 38.13 ± 0.17 | 38.19 ± 0.25 | 38.11 ± 0.42 | 37.94 ± 0.43 | 37.93 ± 0.42 |
| Placebo | 38.14 ± 0.36 | 37.95 ± 0.45 | 38.2 ± 0.44 | 37.99 ± 0.39 | 38.08 ± 0.37 | 37.83 ± 0.41 | 38.08 ± 0.37 | 37.93 ± 0.3 |
| FJ-1 | 38.14 ± 0.44 | 38.04 ± 0.43 | 37.91 ± 0.42 | 37.95 ± 0.21 | 37.93 ± 0.31 | 37.79 ± 0.38 | 38.15 ± 0.39 | 38.16 ± 0.32 |
| FJ-2 | 38.04 ± 0.46 | 37.99 ± 0.29 | 38.09 ± 0.28 | 37.86 ± 0.41 | 38.1 ± 0.4 | 37.84 ± 0.42 | 37.93 ± 0.37 | 38.01 ± 0.34 |
| FJ-3 | 37.91 ± 0.4 | 37.86 ± 0.34 | 37.69 ± 0.23 | 37.96 ± 0.34 | 38.19 ± 0.28 | 38.14 ± 0.42 | 38 ± 0.35 | 38.04 ± 0.37 |
| FJ-4 | 38.16 ± 0.37 | 37.88 ± 0.45 | 38.03 ± 0.47 | 38.19 ± 0.48 | 38.04 ± 0.49 | 37.74 ± 0.25 | 37.76 ± 0.32 | 38.1 ± 0.43 |
| FJ-5 | 37.83 ± 0.3 | 38.01 ± 0.36 | 38.03 ± 0.43 | 38.25 ± 0.15 | 38.03 ± 0.38 | 37.86 ± 0.37 | 37.83 ± 0.36 | 37.79 ± 0.42 |

4.2 Detection Results of Serum ELISA Indexes

The final ELISA results of each group showed that the OPG index of each model group was significantly lower than that of the normal control group (P<0.01), and FJ-1 and FJ-2 had no significant difference compared with the model group (P>0.05). FJ-3 and FJ-4 were extremely different from the model group (P>0.05). FJ-5 had significant difference compared with the model group (P<0.05).

RANKL index of each model group was significantly higher than that of the normal control group (P<0.01), and FJ-1 and FJ-2 had no significant difference compared with the model group (P>0.05). FJ-3, FJ-4 and FJ-5 were extremely different from the model group (P<0.01).

BGP index of each model group was significantly higher than that of the normal control group (P<0.01), and FJ-1, FJ-2, FJ-3 and FJ-5 had no significant difference compared with the model group (P>0.05). FJ-4 had significant difference compared with the model group (P<0.05).

NTX index of each model group was significantly higher than that of the normal control group (P<0.01), and FJ-1, FJ-2 and FJ-5 had no significant difference compared with the model group (P>0.05). There was significant difference between FJ-3 and model group (P<0.05). FJ-4 was extremely different from model group (P<0.01).

TABLE 3

Test results of final blood indexes of rats in each group (n = 8)

|  | Normal | Placebo | FJ-1 | FJ-2 | FJ-3 | FJ-4 | FJ-5 |
|---|---|---|---|---|---|---|---|
| OPG(pg/ml) | 473.14 ± 22.86 | 215.71 ± 84.16 | 218.73 ± 60.61 | 247.46 ± 66.75 | 328.9 ± 40.24 | 355.79 ± 39.04 | 283.21 ± 40.89 |
| RANKL(pg/ml) | 269.13 ± 39.75 | 574.75 ± 32.16 | 557.61 ± 30.08 | 547.11 ± 34.91 | 478.43 ± 31.04 | 455.11 ± 34.2 | 516.63 ± 46.91 |
| BGP(ng/ml) | 20.79 ± 2.82 | 27.33 ± 1.87 | 26.96 ± 2.47 | 26.16 ± 2.82 | 25.53 ± 2.5 | 23.89 ± 3.53 | 24.89 ± 3.94 |
| NTx(nmol/L) | 9.34 ± 0.8 | 14.65 ± 2 | 14.09 ± 1.52 | 13.39 ± 2.31 | 12.74 ± 2.05 | 12.01 ± 0.98 | 13.36 ± 1.48 |
| P value |  |  | 0.47 | 0.21 | 0.00202 | 0.000388 | 0.03032 |
| P value |  |  | 0.14 | 0.06 | 0.00001 | 0.000002 | 0.00593 |
| P value |  |  | 0.37 | 0.17 | 0.06295 | 0.014523 | 0.06805 |
| P value |  |  | 0.27 | 0.13 | 0.03984 | 0.002354 | 0.08248 |

4.3 Determination of Calcium and Phosphorus in Blood and Urine

In each group, the final blood calcium, blood phosphorus, 24-hour urine calcium and urine phosphorus concentration were determined. Compared with the model group, FJ-4 was the most effective, and it could significantly inhibit the loss of calcium and phosphorus. This was followed by FJ-3 and FJ-5.

TABLE 4

Results of final biochemical indexes of rats in each group (n = 8)

|  | Normal | Placebo | FJ-1 | FJ-2 | FJ-3 | FJ-4 | FJ-5 |
|---|---|---|---|---|---|---|---|
| 24 h urine calcium (μmol/L) | 2.48 ± 0.48 | 4.4 ± 0.51 | 4.14 ± 0.65 | 4.18 ± 0.33 | 3.55 ± 0.37 | 3.14 ± 0.26 | 3.89 ± 0.38 |

TABLE 4-continued

Results of final biochemical indexes of rats in each group (n = 8)

|  | Normal | Placebo | FJ-1 | FJ-2 | FJ-3 | FJ-4 | FJ-5 |
|---|---|---|---|---|---|---|---|
| 24 h urine phosphorus (μmol/L) | 2.39 ± 0.6 | 4.52 ± 0.52 | 4.44 ± 0.47 | 4.24 ± 0.46 | 3.49 ± 0.35 | 3.12 ± 0.43 | 3.98 ± 0.32 |
| blood calcium (mmol/L) | 2.17 ± 0.19 | 1.57 ± 0.17 | 1.6 ± 0.14 | 1.68 ± 0.23 | 1.88 ± 0.18 | 1.93 ± 0.23 | 1.69 ± 0.16 |
| blood phosphorus (mmol/L) | 2.35 ± 0.15 | 1.67 ± 0.22 | 1.78 ± 0.09 | 1.77 ± 0.16 | 1.99 ± 0.17 | 2.06 ± 0.08 | 1.72 ± 0.16 |
| P value |  |  | 0.19 | 0.16 | 0.0009 | 0.00001 | 0.01909 |
| P value |  |  | 0.37 | 0.13 | 0.00019 | 0.000021 | 0.01304 |
| P value |  |  | 0.34 | 0.14 | 0.00142 | 0.001328 | 0.06791 |
| P value |  |  | 0.11 | 0.15 | 0.00284 | 0.000163 | 0.29814 |

4.4 Biomechanical Analysis of the Femur

Figure 5:
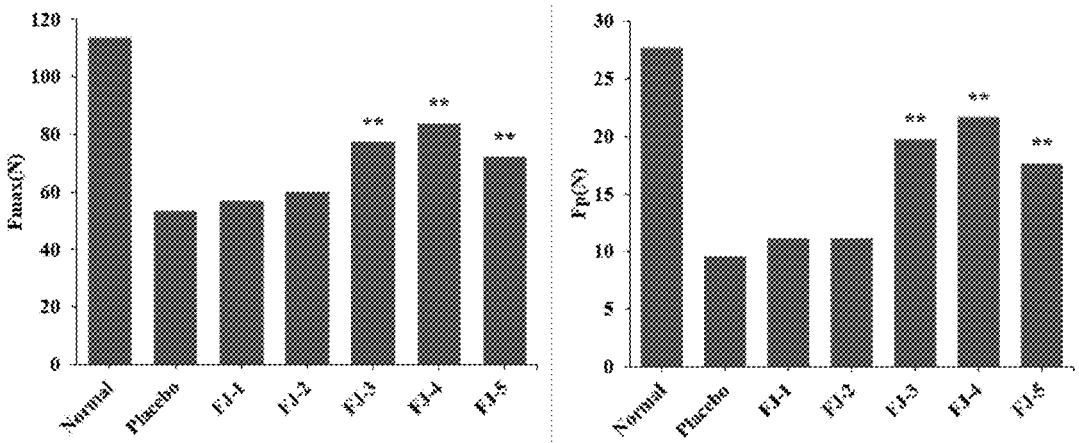
FIG. 5 shows biomechanical test results of final femurs of rats in each group (n=8).
Figure 6:
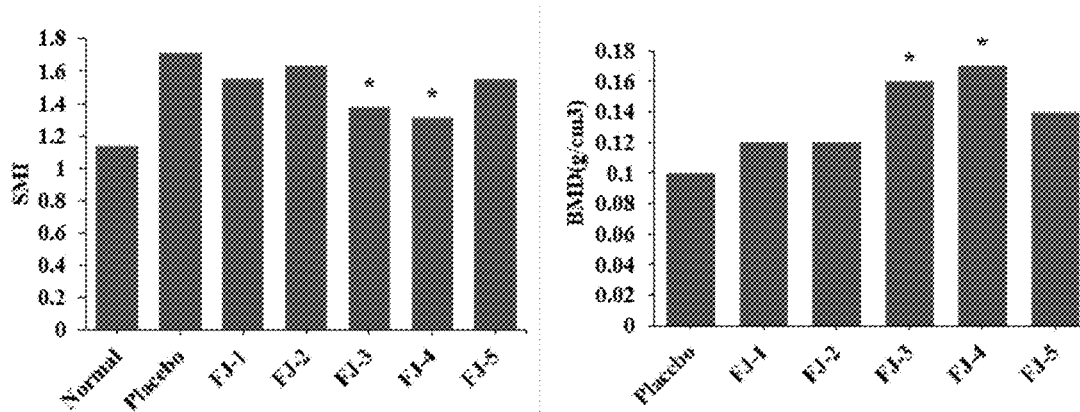
FIG. 6 shows results of micro-CT scan of final femurs of rats in each group (n=8).
Figure 7:
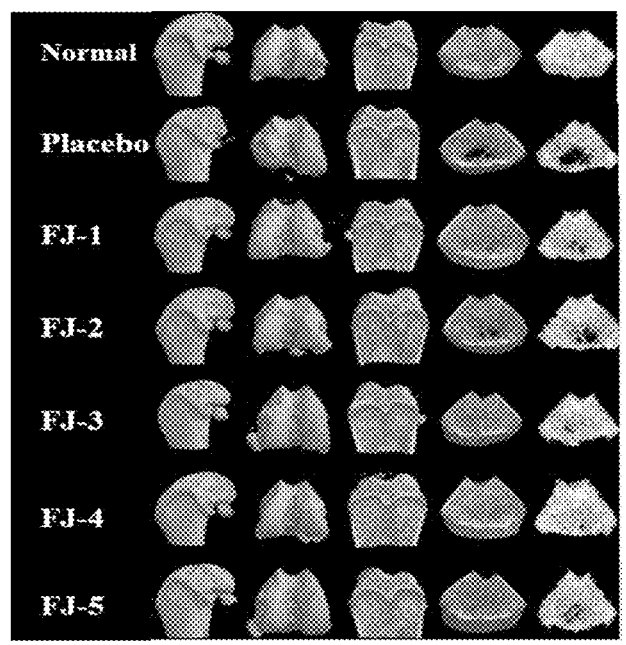
FIG. 7 is a 3D-micro CT scan of final femurs of rats in each group.

The femur specimens of the rats were placed on the biodynamic detection instrument, and the parameters were set as follow. The span was 15 mm, the loading speed was 10 mm/min, the transverse distance was 2~3 mm, the longitudinal distance is 4~5 mm, and the maximum load (Fmax) and the elastic load (Fp) of the femoral sample were recorded by biomechanics, as shown in Table 5. In term of statistical results, the Fmax and F value of femur in the model group were significantly low than those in the normal control group after 8 weeks of glucocorticoid modeling. After drug intervention, FJ-3 and Fj-4 were able to reverse the biomechanical change of femur induce by glucocorticoids, and the effect was best, followed by FJ5 and FJ4. But there was no significant difference compared with FJ-3. The analysis of the differences between each group and the model group were shown in FIG. 5 and Table 5.

TABLE 5

Biomechanical test results of final femur of rats in each group (n = 8)

|  | Normal | Placebo | FJ-1 | FJ-2 | FJ-3 | FJ-4 | FJ-5 |
|---|---|---|---|---|---|---|---|
| Fmax(N) | 113.84 ± 6.37 | 53.41 ± 10.12 | 57.1 ± 9.51 | 60.28 ± 7.55 | 77.26 ± 5.79 | 83.9 ± 8.31 | 72.18 ± 10.16 |
| Fp(N) | 27.7 ± 2.45 | 9.61 ± 2.22 | 11.2 ± 1.29 | 11.21 ± 1.64 | 19.7 ± 5.04 | 21.64 ± 4.6 | 17.69 ± 5.49 |
| P value |  |  | 0.232533 | 0.073226 | <0.001 | <0.001 | 0.001188 |
| P value |  |  | 0.051006 | 0.061727 | <0.001 | <0.001 | <0.001 |

4.5 Analysis of Micro-CT Scanning of Femur

The detection indexes are as follows. Bone volume fraction BV/TV (%): the ratio of the total volume of trabecular bone in the selected area to the total volume of the sample; trabecular thickness Tb.Th (mm): average thickness of trabecular bone; separation of trabecular bone Tb.Sp (mm): average width of medullary cavity between trabeculae; number of trabeculae TB.N (1/mm): number of trabeculae per millimeter; structural model index SMI: inversing trabecular plate-shaped structure or rod-shaped structure, when osteoporosis occurs, trabecular bone changes from plate structure to rod structure, and the value of SMI increases; BMD (g/cm3): the density of cancellous bone in the selected area.

The results showed that the BMD of the model group was significantly lower than that of the normal control group, and the SMI index of the model group was significantly higher than that of the normal control group. After drug intervention, the effect of FJ-4 was best, which was significantly improved compared with the model group, followed by FJ-3 group, with significant differences compared with the model group (P<0.05).

TABLE 6

| Group | BV/TV (%) | Tb.Th (mm) | Tb.Sp (mm) | Tb.N (1/mm) | SMI | BMD (g/cm$^3$) |
|---|---|---|---|---|---|---|
| Normal | 37.11 ± 2.57 | 0.11 ± 0 | 0.24 ± 0.03 | 3.23 ± 0.3 | 1.14 ± 0.13 | 0.22 ± 0.01 |
| Placebo | 19.57 ± 5.68 | 0.09 ± 0.01 | 0.43 ± 0.13 | 2.4 ± 0.48 | 1.71 ± 0.21 | 0.1 ± 0.04 |
| FJ-1 | 22.51 ± 3.51 | 0.1 ± 0 | 0.44 ± 0.1 | 2.27 ± 0.22 | 1.55 ± 0.13 | 0.12 ± 0.02 |
| FJ-2 | 21.42 ± 2.01 | 0.1 ± 0.01 | 0.42 ± 0.03 | 2.28 ± 0.17 | 1.63 ± 0.08 | 0.12 ± 0.02 |
| FJ-3 | 27.36 ± 2.09 | 0.11 ± 0.01 | 0.32 ± 0.04 | 2.77 ± 0.18 | 1.38 ± 0.1 | 0.16 ± 0.01 |
| FJ-4 | 31.13 ± 2.07 | 0.1 ± 0 | 0.28 ± 0.03 | 2.95 ± 0.21 | 1.31 ± 0.1 | 0.17 ± 0.01 |
| FJ-5 | 24.56 ± 1.88 | 0.1 ± 0 | 0.36 ± 0.05 | 2.47 ± 0.19 | 1.55 ± 0.11 | 0.14 ± 0.01 |

Micro-CT scanning results of final femur of rats in each group (n = 8)

Described above are merely illustrative of the disclosure to enable those skilled in the art to implement or use the disclosure, and are not intended to limit the disclosure. It should be understood that any modifications, replacements or changes made by those skilled in the art without departing from the spirit of the disclosure should fall within the scope of the disclosure.

We claim:

1. A capsule consisting essentially of 30.768%-68.179% by weight of chicken cartilage collagen; 6.249%~18.750% by weight of magnesium; 0.002%~0.0067% by weight of vitamin k2; 0.00006%~0.00099% by weight of vitamin D3; 1~300 parts by weight of *Eucommia* bark, 1~150 parts by weight of *Eucommia* leaves, 1-100 parts by weight of Rhizoma Drynariae, and 1-50 parts by weight of Semen Cuscutae.

* * * * *